United States Patent
Otani et al.

(10) Patent No.: US 10,199,148 B2
(45) Date of Patent: Feb. 5, 2019

(54) PARTICLE BEAM IRRADIATION EQUIPMENT

(71) Applicant: MITSUBISHI ELECTRIC CORPORATION, Chiyoda-ku, Tokyo (JP)

(72) Inventors: Toshihiro Otani, Tokyo (JP); Takaaki Iwata, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 0 days.

(21) Appl. No.: 15/515,345

(22) PCT Filed: Nov. 28, 2014

(86) PCT No.: PCT/JP2014/081515
§ 371 (c)(1),
(2) Date: Mar. 29, 2017

(87) PCT Pub. No.: WO2016/084218
PCT Pub. Date: Jun. 2, 2016

(65) Prior Publication Data
US 2017/0236631 A1 Aug. 17, 2017

(51) Int. Cl.
*H01F 7/00* (2006.01)
*H01F 7/20* (2006.01)
(Continued)

(52) U.S. Cl.
CPC ............... *H01F 7/20* (2013.01); *A61N 5/10* (2013.01); *A61N 5/1075* (2013.01); *G21K 1/093* (2013.01);
(Continued)

(58) Field of Classification Search
CPC ........... H01F 7/20; A61N 5/10; A61N 5/1075; A61N 5/1043; A61N 2005/1087;
(Continued)

(56) References Cited

U.S. PATENT DOCUMENTS

| 2007/0273464 A1 | 11/2007 | Kitahara et al. |
| 2011/0220809 A1 | 9/2011 | Yajima et al. |
| 2016/0074676 A1 | 3/2016 | Yajima et al. |

FOREIGN PATENT DOCUMENTS

| JP | 6-163197 A | 6/1994 |
| JP | 6-310300 A | 11/1994 |

(Continued)

OTHER PUBLICATIONS

International Search Report (PCT/ISA/210) dated Mar. 3, 2015, by the Japanese Patent Office as the International Searching Authority for International Application No. PCT/JP2014/081515.
Written Opinion (PCT/ISA/237) dated Mar. 3, 2015, by the Japanese Patent Office as the International Searching Authority for International Application No. PCT/JP2014/081515.
(Continued)

*Primary Examiner* — Nicole Ippolito
*Assistant Examiner* — Hanway Chang
(74) *Attorney, Agent, or Firm* — Buchanan Ingersoll & Rooney PC

(57) ABSTRACT

In particle beam irradiation equipment, a control unit causes a storage unit to store, as position information of reference positions, position information of electromagnets that is acquired at the time of their first alignment, by cameras, and then acquires displacement amounts, based on the position information of the reference positions stored in the storage unit and from position information of the electromagnets acquired at the time of their realignment, by the cameras.

13 Claims, 9 Drawing Sheets

(51) Int. Cl.
*A61N 5/10* (2006.01)
*G21K 5/04* (2006.01)
*H05H 7/04* (2006.01)
*G21K 1/093* (2006.01)
*H05H 13/04* (2006.01)

(52) U.S. Cl.
CPC ............... *G21K 5/04* (2013.01); *H05H 7/04* (2013.01); *H05H 13/04* (2013.01); *A61N 5/1043* (2013.01); *A61N 2005/1087* (2013.01); *H05H 2245/122* (2013.01); *H05H 2277/10* (2013.01)

(58) Field of Classification Search
CPC ............ G21K 1/093; G21K 5/04; H05H 7/04; H05H 13/04; H05H 2245/122; H05H 2277/10
USPC ................................ 250/492.1, 492.2, 492.3
See application file for complete search history.

(56) References Cited

FOREIGN PATENT DOCUMENTS

| | | |
|---|---|---|
| JP | 11-137699 A | 5/1999 |
| JP | H11-137699 A | 5/1999 |
| JP | 2006-302818 A | 11/2006 |
| JP | 2006-344466 A | 12/2006 |
| JP | 2007-149405 A | 6/2007 |
| JP | 2009-217938 A | 9/2009 |
| JP | 2011-182987 A | 9/2011 |

OTHER PUBLICATIONS

European Search Report dated Apr. 23, 2018 issued by the European Patent Office in corresponding European Patent Application 149070831. (8 pages).

Chinese Office Action dated Apr. 4, 2018 issued by the People's Republic of China State Intellectual Property Office in corresponding Patent Application No. 201480083323.X (13 pages) with English language translation.

PARTICLE BEAM IRRADIATION EQUIPMENT

TECHNICAL FIELD

The present invention relates to particle beam irradiation equipment which can precisely control the position, attitude and the like, of an electromagnet used in a particle beam irradiation system.

BACKGROUND ART

In conventional particle beam irradiation systems, it is general that an accelerator such as a synchrotron or the like and a treatment room are placed on the same plane. In recent years, in association with enlargement of the particle beam irradiation systems, deformation of the building thereof occurs due to seasonal variation in outside air temperature or due to crustal movement such as ground depression or the like, resulting in wrong alignment and thus in failure of the radiated beam to meet a prescribed performance. In order to deal therewith, in the use of the particle beam irradiation system, there has arisen a need to change its operation parameters for every season, or to periodically execute re-adjustment of the positions, attitudes and the like, of the electromagnets and the like. As a method of establishing alignment at the time of installation of the particle beam irradiation system, there is disclosed a method in which alignment is established after a displacement amount from a preset position, which is given as a reference point in the building or on the apparatus, is calculated (see, for example, Patent Document 1 and Patent Document 2). Meanwhile, in the case where the particle beam irradiation facility is constructed on a narrow ground adjacent to a hospital or the like, a structure in which the accelerator and the treatment room are arranged in vertical relation therebetween, or something like that, is likely to be employed (see, for example, patent Document 3).

CITATION LIST

Patent Document

Patent Document 1: Japanese Patent Application Laid-open No. 2006-344466 (Paragraph 0024, FIG. 2)
Patent Document 2: Japanese Patent Application Laid-open No. 2006-302818 (Paragraph 0025, FIG. 2)
Patent Document 3: Japanese Patent Application Laid-open No. 2011-182987 (Paragraph 0032, FIG. 1)

SUMMARY OF THE INVENTION

Problems to be Solved by the Invention

In the case where the accelerator and the treatment room are arranged in vertical relation therebetween, there is a problem that the structure of the building becomes complex, resulting in large deformation of the building due to temperature variation between seasons, or the like. In particular, in the case where the accelerator or a beam-transport-system apparatus is arranged above the treatment room, there is a problem that the deformation is more remarkable than otherwise, because a floor on which such an apparatus is arranged, is placed apart from a building foundation part strengthened by foundation improvement or by piling, so that an interspace by the treatment room or the like, exists under the floor on which the apparatus is placed. Further, with respect to the beam-transport-system apparatus, because the electromagnets for controlling transportation of the beam are placed respectively on different floors, there is a problem that it is difficult to precisely control the relative positions and attitudes of the electromagnets.

This invention has been made to solve the problems as described above, and an object thereof is to provide particle beam therapy equipment which makes highly-precise beam irradiation possible, not only when the accelerator or the like and the treatment room in the particle beam irradiation system are placed on the same plane, but also when they are arranged in vertical relation therebetween.

Means for Solving the Problems

The particle beam irradiation equipment of the invention comprises: a first electromagnet provided on an upstream side of a high-energy-beam irradiation-system line; a second electromagnet provided on a downstream side of the high-energy-beam irradiation-system line; a position information acquisition unit that acquires position information of the first electromagnet and the second electromagnet; a storage unit in which the position information of the first electromagnet and the second electromagnet at the time of their first alignment, is prestored as reference position information; an adjustment mechanism that adjusts positions and attitudes of the first electromagnet and the second electromagnet; and a control unit that calculates, based on the reference position information stored in the storage unit, and from position information of the first electromagnet and the second electromagnet acquired at the time of their realignment by the position information acquisition unit, displacement amounts of positions and attitudes of the first electromagnet and the second electromagnet occurring from the time of the first alignment to the time of the realignment, and controls/adjusts using the adjustment mechanism, the positions and attitudes of the first electromagnet and the second electromagnet according to the displacement amounts.

Effect of the Invention

According to this invention, the reference position information of the first electromagnet provided on the upstream side of the high-energy-beam irradiation-system line and the second electromagnet provided on the downstream side thereof, is prestored in the storage unit, and then the positions and attitudes of the first electromagnet and the second electromagnet are adjusted at the time of their realignment, on the basis of the reference position information stored in the storage unit. Thus, it is possible to easily adjust the positions and attitudes of the electromagnets even if the building deforms due to seasonal variation in outside air, crustal movement or the like.

MODES FOR CARRYING OUT THE INVENTION

Embodiment 1

Figure 1:
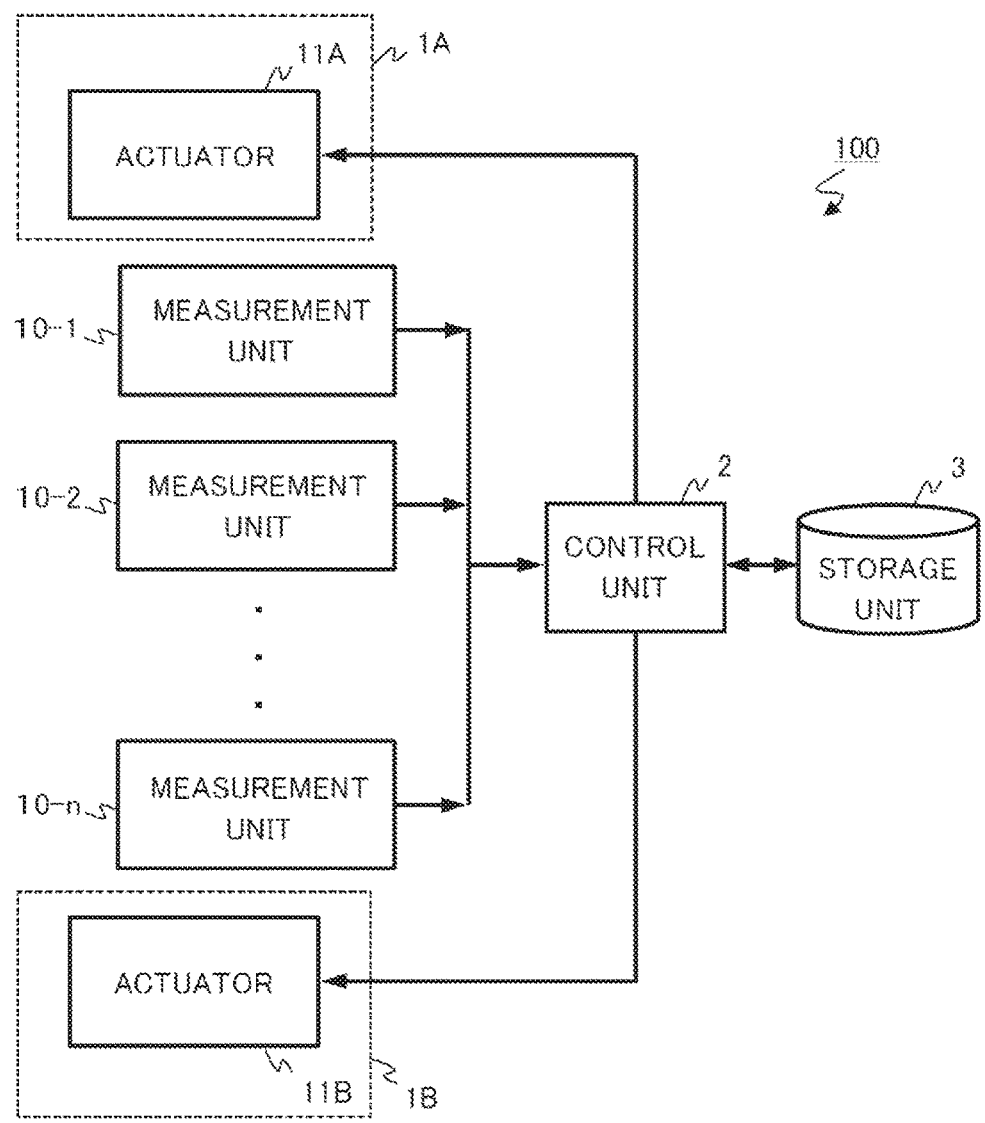
FIG. 1 is a block diagram showing a configuration of particle beam irradiation equipment according to Embodiment 1 of the invention.
Figure 2:
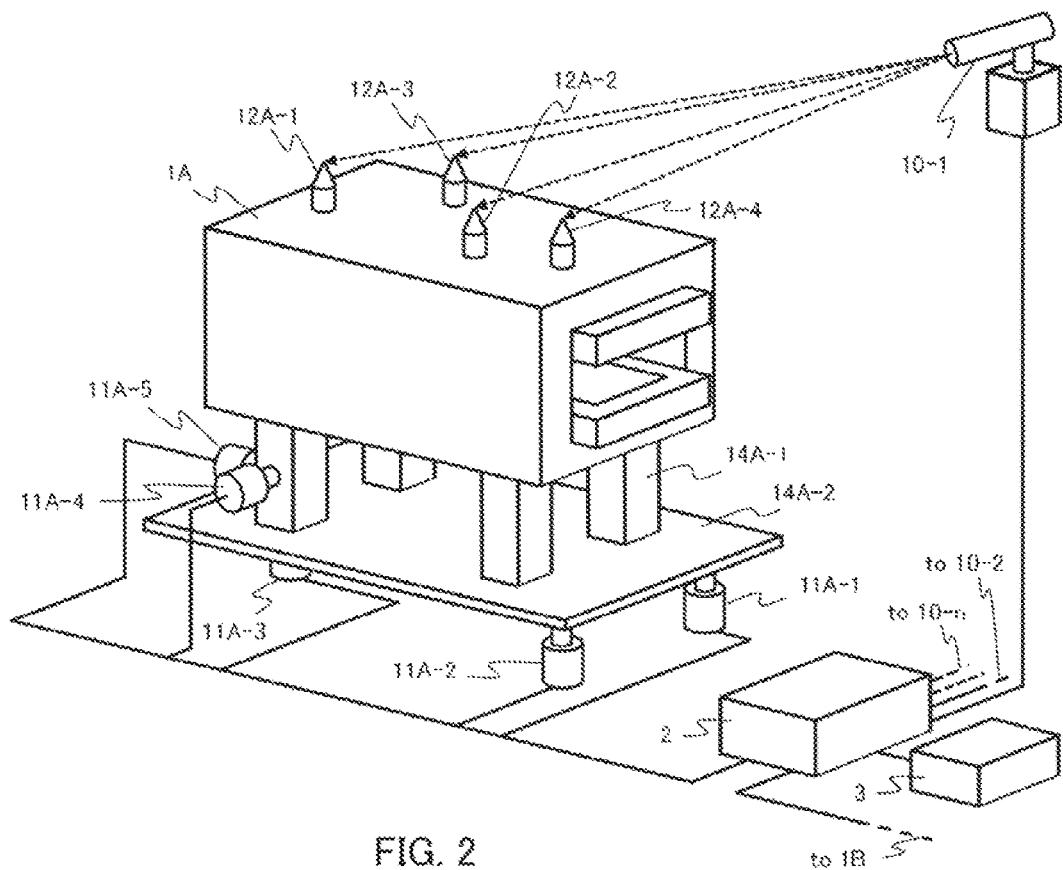
FIG. 2 is a perspective view showing an external appearance of the particle beam irradiation equipment according to Embodiment 1 of the invention.

FIG. 1 is a block diagram showing a configuration of particle beam irradiation equipment 100 according to Embodiment 1 of the invention. FIG. 2 is an external view of an electromagnet 1A for particle beam irradiation system, which is provided with the particle beam irradiation equipment 100.

As shown in FIG. 1 and FIG. 2, the particle beam irradiation equipment 100 is configured with: a plurality of cameras 10 (10-1, 10-2, . . . , 10-$n$ [n denotes an integer]) serving as a measurement unit which is a position information acquisition unit for acquiring position information about positions, attitudes and the like, of electromagnets 1 (1A, 1B); a storage unit 3 in which the position information of the electromagnets 1 (1A, 1B) at the time of installation of the particle beam irradiation system is stored as reference positions; a control unit 2 for acquiring measured positions of the electromagnets 1 (1A, 1B) measured by the cameras 10 and the reference positions of the electromagnets 1 (1A, 1B) stored in the storage unit 3, to thereby output control information; and actuators 11 (11A, 11B) serving as an adjustment mechanism for adjusting the positions and attitudes of the electromagnets 1 according to the control information from the control unit 2.

In order to measure the relative positions and attitudes of the first electromagnet 1A and the second electromagnet 1B that are placed at two positions apart from each other, stereo cameras are used as the cameras 10. However, in the case of the particle beam irradiation system in which the accelerator and the irradiation room are placed on different floors in the building, the electromagnet 1A and the electromagnet 1B that are main electromagnets at two places in the line of a high-energy-beam irradiation system (referred also to as High-Energy Beam Transport (hereinafter, HEBT) System), go beyond the view of one of the camera 10. For this reason, ingenuity is required in the measurement using the cameras 10.

In Embodiment 1 of the invention, in order to solve the aforementioned problem on the view of the camera, the following method is used. Here, it is assumed that the measurement is made on the main electromagnet 1A placed on the upstream side of the HEBT system line and the other main electromagnet 1B placed on the downstream side of the HEBT system line. Using one camera 10-1, the positions of targets 12A (12A-1, 12A-2, 12A-3, 12A-4) formed on the electromagnet 1A are measured. Then, using another camera 10-2, the positions of targets 12B (12B-1, 12B-2, 12B-3, 12B-4) formed on the electromagnet 1B are measured. However, if nothing is then done, what has just been done is that the position and attitude of the electromagnet 1A have been expressed on a coordinate system (x, y, z) that the camera 10-1 has, while the position and attitude of the electromagnet 1B have been expressed on a coordinate system (X, Y, Z) that the camera 10-2 has. The relative relationship in position and attitude between the electromagnet 1A and the electromagnet 1B are unknown.

Figure 3:
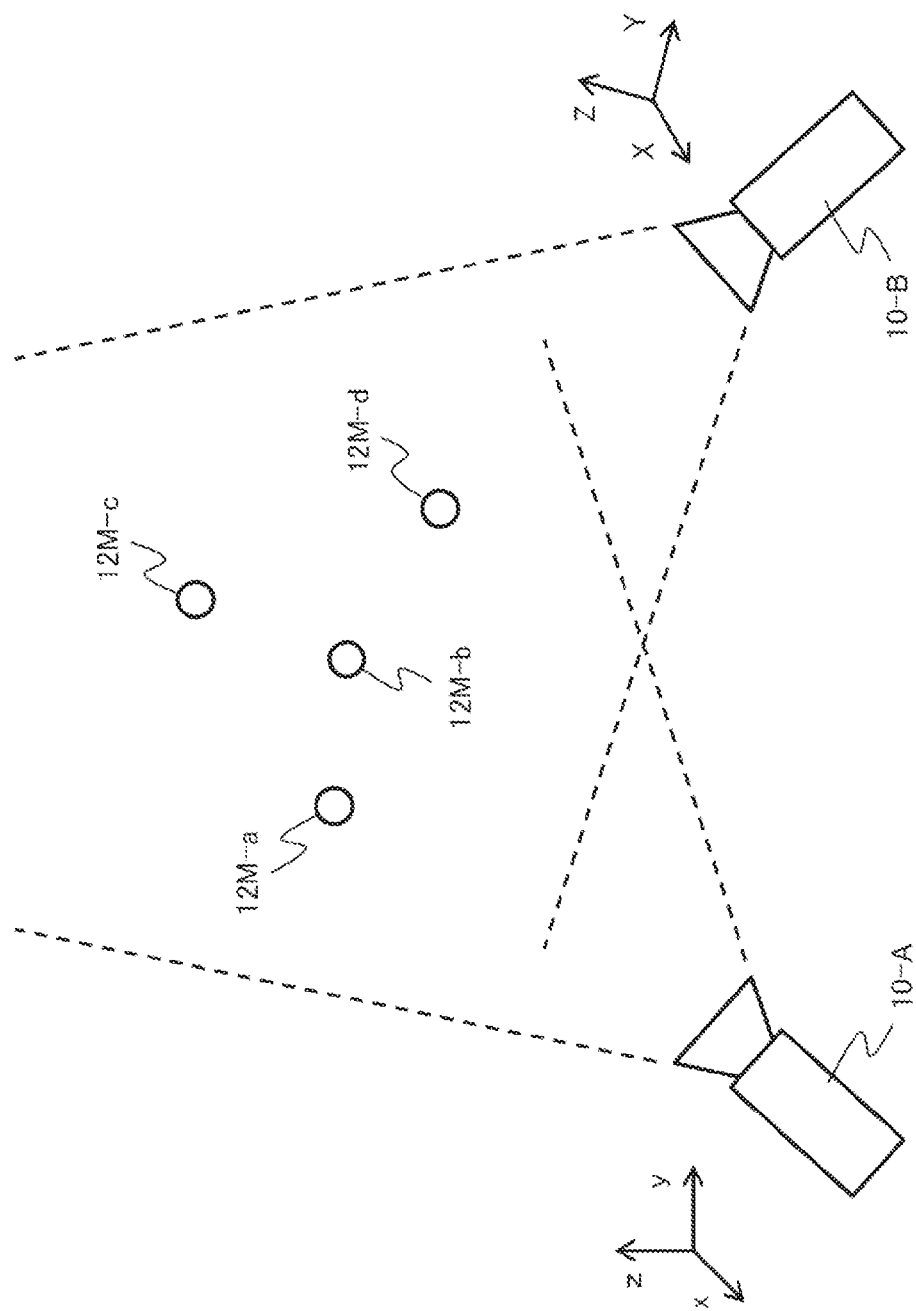
FIG. 3 is a diagram illustrating an adjusting method by the particle beam irradiation equipment according to Embodiment 1 of the invention.

In this regard, as shown in FIG. 3, if an overlapping portion exists between the views of the camera 10-A and the camera 10-B2 and at least four number (or three number, in a two-dimensional case) of coordinate-conversion purpose targets 12M (12M-a, 12M-b, 12M-c, 12M-d) can be placed at different positions within the overlapping portion, it is possible to determine a coordinate conversion formula for converting the coordinate system on the camera 10-A into the coordinate system on the camera 10-B, from information of coordinates on the camera 10-A about the four targets 12M (12M-a, 12M-b, 12M-c, 12M-d) and information of coordinates on the camera 10-B about the targets.

Specifically, description is given as follows.

The coordinate conversion formula for converting the coordinate system (x, y, z) on the camera 10-A into the coordinate system (X, Y, Z) on the camera 10-B has a structure of a following formula.

[Mathematical 1]

$$\overset{q}{\begin{bmatrix} X \\ Y \\ Z \end{bmatrix}} = \overset{T}{\begin{bmatrix} T_{11} & T_{12} & T_{13} \\ T_{21} & T_{22} & T_{23} \\ T_{31} & T_{32} & T_{33} \end{bmatrix}} \overset{p}{\begin{bmatrix} x \\ y \\ z \end{bmatrix}} + \overset{O}{\begin{bmatrix} O_1 \\ O_2 \\ O_3 \end{bmatrix}} \quad (1)$$

In order to finally determine the coordinate conversion formula (1), it is required to calculate the twelve number of unknown parameters $T_{11}, \ldots, T_{33}, O_1, \ldots, O_3$.

Applying the formula (1) to the respective coordinate-conversion purpose targets 12M (12M-a, 12M-b, 12M-c, 12M-d) comes down to the issue of solving the simultaneous equations comprising four formulae. When the four formulae are bundled together using matrix expression, they can be expressed as follows.

[Mathematical 2]

$$\begin{bmatrix} \vdots & \vdots & \vdots & \vdots \\ q_1 & q_2 & q_3 & q_4 \\ \vdots & \vdots & \vdots & \vdots \end{bmatrix} = \begin{bmatrix} T & | & O \end{bmatrix} \begin{bmatrix} \vdots & \vdots & \vdots & \vdots \\ p_1 & p_2 & p_3 & p_4 \\ \vdots & \vdots & \vdots & \vdots \\ \hline 1 & 1 & 1 & 1 \end{bmatrix} \quad (2)$$

$$\therefore \begin{bmatrix} T & | & O \end{bmatrix} = \begin{bmatrix} \vdots & \vdots & \vdots & \vdots \\ q_1 & q_2 & q_3 & q_4 \\ \vdots & \vdots & \vdots & \vdots \end{bmatrix} \begin{bmatrix} \vdots & \vdots & \vdots & \vdots \\ p_1 & p_2 & p_3 & p_4 \\ \vdots & \vdots & \vdots & \vdots \\ \hline 1 & 1 & 1 & 1 \end{bmatrix}^{-1}$$

Further, in the case of seeking to get coordinate conversion using four or more number of the targets in consideration of a measurement error or the like, it is conceivable to use least-square method for seeking.

[Mathematical 3]

$$\begin{bmatrix} T & \vdots & O \end{bmatrix} = \begin{bmatrix} \vdots & \vdots & & \vdots \\ q_1 & q_2 & \cdots & q_n \\ \vdots & \vdots & & \vdots \end{bmatrix} \begin{bmatrix} \vdots & \vdots & & \vdots \\ p_1 & p_2 & \cdots & p_n \\ \vdots & \vdots & & \vdots \\ \hline 1 & 1 & 1 & 1 \end{bmatrix}^T \left( \begin{bmatrix} \vdots & \vdots & & \vdots \\ p_1 & p_2 & \cdots & p_n \\ \vdots & \vdots & & \vdots \\ \hline 1 & 1 & 1 & 1 \end{bmatrix} \begin{bmatrix} \vdots & \vdots & & \vdots \\ p_1 & p_2 & \cdots & p_n \\ \vdots & \vdots & & \vdots \\ \hline 1 & 1 & 1 & 1 \end{bmatrix}^T \right)^{-1} \quad (3)$$

It is noted that the superscript T is indicative of a transposed matrix.

Figure 4:
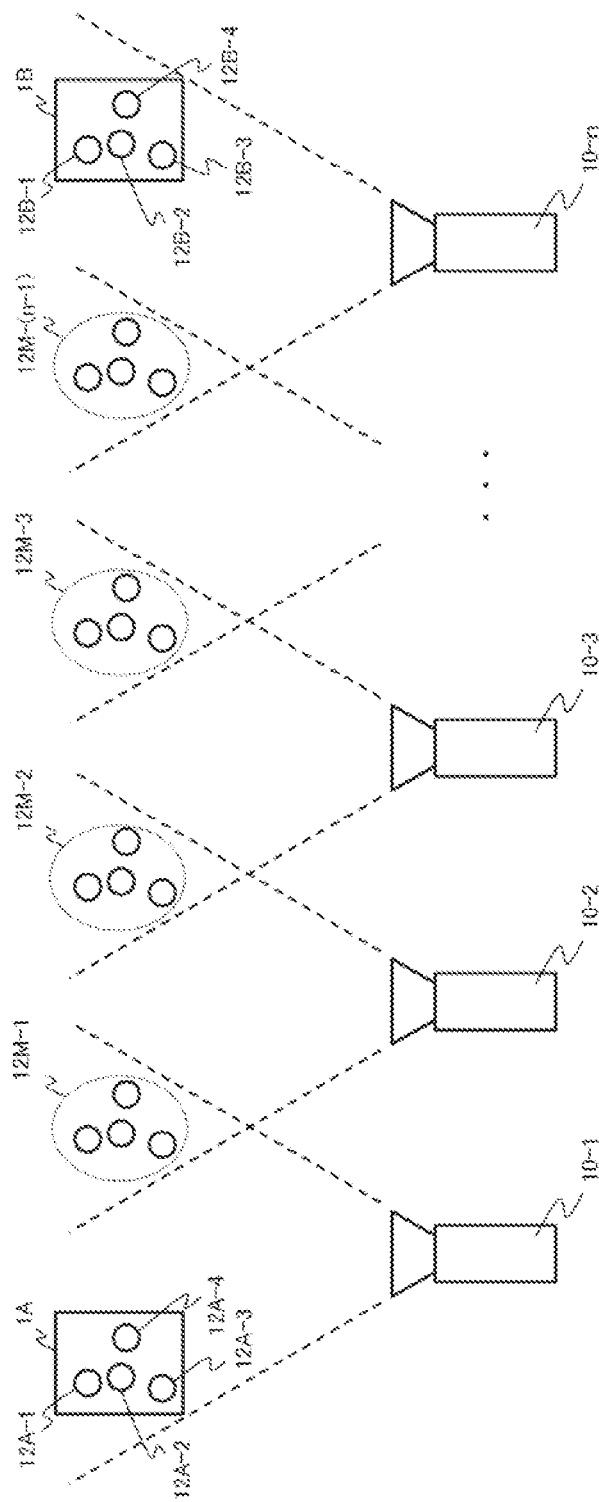
FIG. 4 is a diagram illustrating how to acquire position information by the particle beam irradiation equipment according to Embodiment 1 of the invention.

In the case where no overlapping portion exists between the views of the camera 10-A and the camera 10-B, as shown in FIG. 4, it is conceivable to additionally prepare another plurality of cameras, and to link the camera 10-1 to the camera 10-$n$ to each other in a row so that overlapping portions exist each in a small degree between their respective views. In each location where the views of the adjacent cameras are overlapped, each set of coordinate-conversion purpose targets 12M-1, 12M-2, . . . , or 12M-(n−1) each comprising four targets, is placed and then subjected to measurement. This finally makes it possible to determine, using coordinate conversion of the coordinate systems of the respective cameras, the coordinate conversion formula from the coordinate system (x1, y1, z1) on the camera 10-1 to the coordinate system (xn, yn, zn) on the camera 10-$n$.

In this manner, when the coordinate systems are made matched to each other using the plurality of cameras 10 (10-1, 10-2, . . . 10-$n$), even if the main electromagnet 1A placed on the upstream side of the HEBT system line and the other main electromagnet 1B placed on the downstream side of the HEBT system line are positioned on different floors in the building, it is possible to measure the relative positions and attitudes of the electromagnet 1A and the electromagnet 1B.

The storage unit 3 is configured with a storage medium such as a hard disk, a removable disk, a memory or the like, in which, at the time of installation of the particle beam irradiation system (at the time of first alignment), position information about positions, attitudes and the like, of the electromagnets 1 measured by the cameras 10 is stored as the reference positions.

The control unit 2 acquires, using the cameras 10, the position information about the positions, attitudes and the like, of the electromagnets 1 (1A, 1B) at their first alignment, and stores it in the storage unit 3 as reference positions. Further, the control unit 2 acquires, using the cameras 10, position information about positions, attitudes and the like, of the electromagnets 1 (1A, 1B) at their realignment, and compares it with the position information of the electromagnets 1 as the reference positions taken out from the storage unit 3, to thereby calculate displacement amounts or the like, due to deformation of the building or the like, and then adjusts the positions and attitudes of the electromagnets 1 by controlling the actuators 11 according to the control information, such as the calculated displacement amounts or the like. The control unit 2 can be implemented using a general-purpose computer system or the like (for example, a personal computer).

The actuators 11 are mounted on pedestals 14 (14A-1, 14A-2, 14B-1, 14B-2) of the electromagnets 1. As shown in FIG. 2, the actuators 11A (or 11B) comprise actuators (11A(B)-1, 11A(B)-2, 11A(B)-3) for a vertical direction and actuators (11A(B)-4, 11A(B)-5) for two horizontal directions, and are thus mounted corresponding to total three directions (six degrees of freedom). The actuators 11 (11A, 11B) are actuated according to the control information from the control unit 2.

Figure 5:
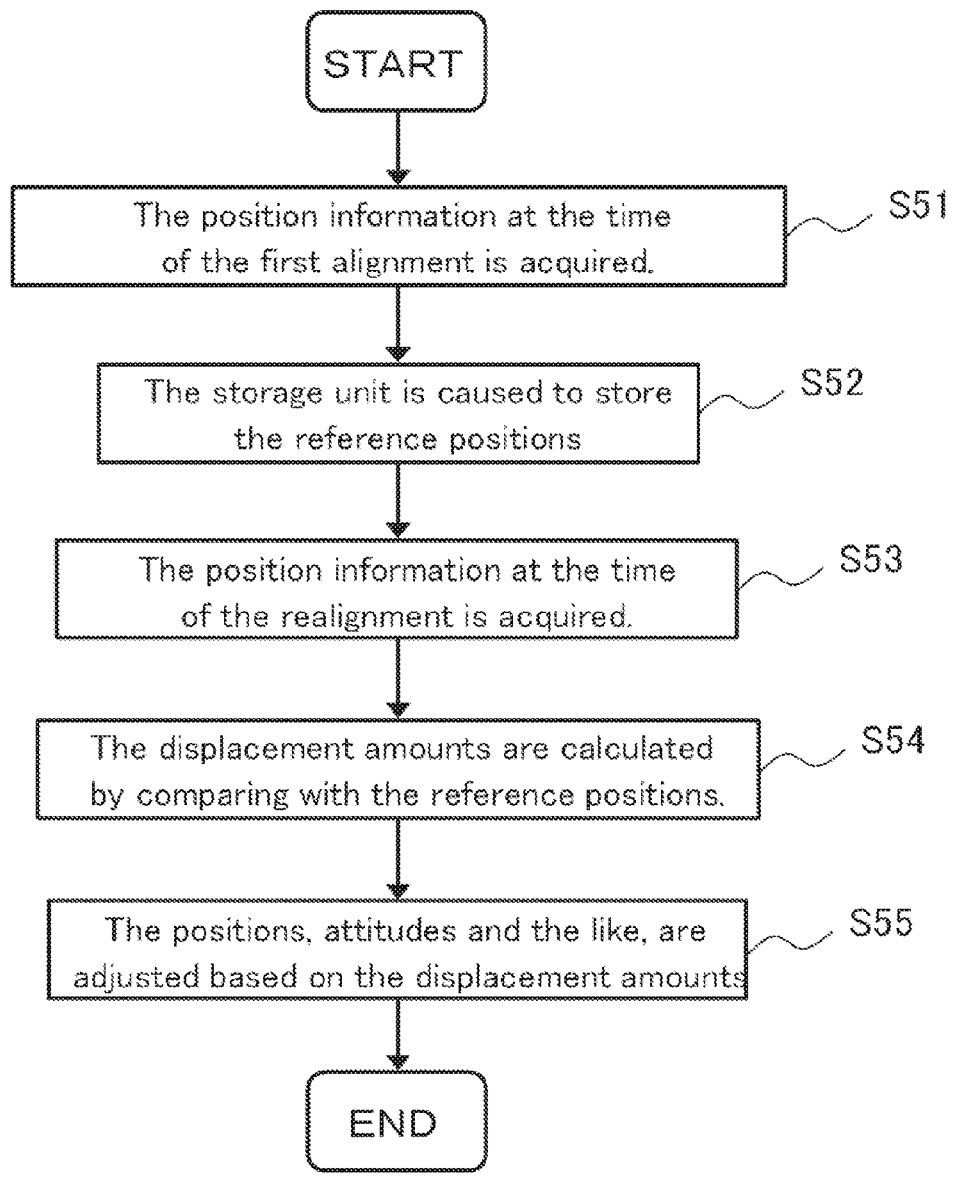
FIG. 5 is a flowchart illustrating a method of controlling a position and an attitude by the particle beam irradiation equipment according to Embodiment 1 of the invention.

Next, operations of the particle beam irradiation equipment 100 according to Embodiment 1 of the invention will be described using FIG. 5. FIG. 5 is a flowchart illustrating the operations of the particle beam irradiation equipment 100.

As shown in FIG. 5, at the time of the first alignment, firstly, the control unit 2 of the particle beam irradiation equipment 100 measures, using the cameras 10 (10-1, 10-2, . . . , 10-$n$), positions of the four targets 12A-1, 12A-2, 12A-3, 12A-4 placed on each of the electromagnets 1 (1A, 1B). From data of coordinates of thus-obtained positions, the positions, attitudes and the like, of the electromagnets 1 (1A, 1B) are calculated, so that the position information at the time of the first alignment is acquired (Step S51).

Subsequently, the control unit 2 causes the storage unit 3 to store the position information of the electromagnets 1 (1A, 1B) at the time of the first alignment that is acquired in Step S51, as position information of the reference positions of the electromagnets 1 (1A, 1B) (Step S52). At this time, even if the main electromagnet 1A that is placed on the upstream side and the electromagnet 1B that is placed on the downstream side are distantly positioned, the position information is given as relative reference positions, when the plurality of cameras 10-1, 10-2, . . . , 10-$n$ is used; the coordinate-conversion purpose targets 12M-1, 12M-2, . . . , 12M-(n−1) are placed in each location where the views of the adjacent cameras are overlapped and are then subjected to measurement; and the position information is determined after the coordinate axes of the electromagnet 1A and the electromagnet 1B are matched to each other.

Then, when alignment is performed again because of deformation of the building due to seasonal variation in outside air temperature, crustal movement or the like, the control unit 2 again measures, using the cameras 10 (10-1, 10-2, . . . , 10-$n$), positions of the four targets 12A-1, 12A-2, 12A-3, 12A-4 placed on each of the electromagnets 1 (1A, 1B). From data of coordinates of thus-obtained positions, the positions, attitudes and the like, of the electromagnets 1 (1A, 1B) are calculated, so that the position information at the time of the realignment is acquired (Step S53).

When the position information at the time of the realignment of the electromagnets 1 (1A, 1B) is acquired in Step S53, the control unit 2 then takes out the position information of the reference positions from the storage unit 3, to thereby calculate the displacement amounts by comparing the position information at the time of the realignment of the electromagnets 1 (1A, 1B) with the position information of the reference positions (Step S54). At this time, even if the electromagnet 1A and the electromagnet 1B are distantly positioned, when, like in the case of the first alignment, the plurality of cameras 10-1, 10-2, . . . , 10-$n$ is used to measure the coordinate-conversion purpose targets 12M-1, 12M-2, . . . , 12M-(n–1) placed in each location where the views of the adjacent cameras are overlapped, and the relative position information is given after the coordinate axes of the electromagnet 1A and the electromagnet 1B are matched to each other, it is possible to highly precisely find the displacement amounts, because the relative positional relationship of the electromagnet 1A and the electromagnet 1B is determined on a comparison basis with the reference positions.

Lastly, based on the thus-obtained displacement amounts of the electromagnets 1 (1A, 1B), the control unit 2 outputs control information such as an actuation amount or the like, to any one of the actuators of the electromagnets 1 (1A, 1B) for the vertical direction (11A-1, 11A-2, 11A-3, 11B-1, 11B-2, 11B-3) and the actuators thereof for the horizontal directions (11A-4, 11A-5, 11B-4, 11B-5), to thereby instruct it to cause actuation, so that the positions, attitudes and the like, of the electromagnets 1 (1A, 1B) are adjusted.

As described above, in the particle beam irradiation equipment 100 according to Embodiment 1 of the invention, the control unit 2 causes the storage unit 3, at the time of the first alignment, to store the position information of the electromagnets 1 (1A, 1B) acquired by the cameras 10 (10-1, 10-2, . . . , 10-$n$) as position information of the reference positions, and then acquires the displacement amounts, based on the position information of the reference positions stored in the storage unit 3, from the position information of the electromagnets 1 (1A, 1B) acquired by the cameras 10 (10-1, 10-2, . . . , 10-$n$) at the time of the realignment. Thus, it is possible to easily adjust the positions, attitudes and the like, of the electromagnets even if the building deforms due to seasonal variation in outside air, crustal movement or the like.

In addition, because the relative position information is acquired using the plurality of cameras 10 (10-1, 10-2, . . . , 10-$n$), even if the main electromagnet placed on the upstream side of the HEBT system line and the electromagnet placed on the downstream side thereof are distantly positioned, for example, they are placed on different floors in the building, it is possible to precisely adjust the electromagnets while keeping their relative positions, attitudes and the like. This makes it possible to achieve highly-precise beam irradiation.

Embodiment 2

In Embodiment 1, a case has been shown in which the position information at the time of the realignment is acquired by the cameras 10, whereas in Embodiment 2, a case will be shown in which that information is acquired by simulation.

Figure 6:
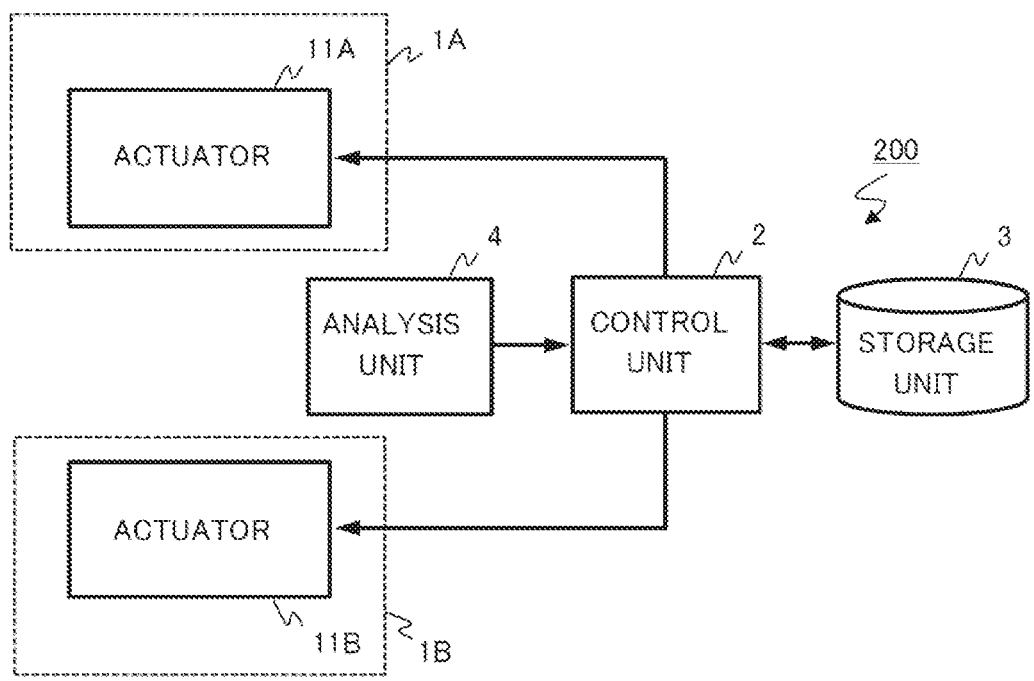
FIG. 6 is a block diagram showing a configuration of particle beam irradiation equipment according to Embodiment 2 of the invention.
Figure 7:
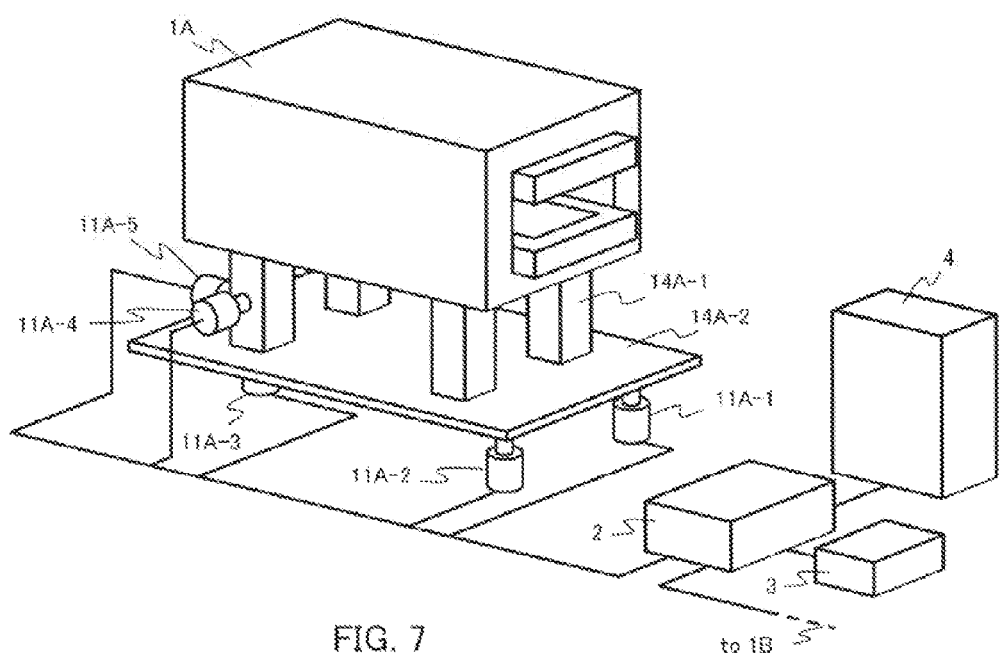
FIG. 7 is a perspective view showing an external appearance of the particle beam irradiation equipment according to Embodiment 2 of the invention.

FIG. 6 is a block diagram showing a configuration of particle beam irradiation equipment 200 according to Embodiment 2 of the invention. FIG. 7 is an external view of an electromagnet for particle beam irradiation system, which is provided with the particle beam irradiation equipment 200.

As shown in FIG. 6 and FIG. 7, the particle beam irradiation equipment 200 includes a deformation simulator 4 serving as an analysis unit, in place of the cameras 10 (10-1, 10-2, . . . , 10-$n$) serving as a measurement unit in Embodiment 1. The deformation simulator 4 carries out deformation simulation using, for example, a finite element analysis in which the building, the apparatuses and the like, are all modelized. At the time of the first alignment, the control unit 2 causes the storage unit 3 to prestore the position information about the measured positions, attitudes and the like, of the electromagnets 1 (1A, 1B), and at the time of the realignment, the control unit calculates, using the deformation simulator 4, deformation amounts of the building, the apparatuses and the like, to thereby acquire position information of the electromagnets 1 (1A, 1B) at the time of the realignment, based on the position information as the reference positions stored in the storage unit 3.

In this manner, when all the deformation amounts of the building, the apparatuses and the like, at the time of the realignment, are calculated using the deformation simulator 4 and the position information is acquired therefrom, even if the main electromagnet 1A placed on the upstream side of the HEBT system line and the other main electromagnet 1B placed on the downstream side of the HEBT system line are positioned on different floors in the building, it is possible to easily recognize the relative positions, attitudes and the like, of the electromagnet 1A and the electromagnet 1B, and it is possible to highly precisely find the displacement amounts because the relative positional relationship of the electromagnet 1A and the electromagnet 1B is determined on a comparison basis with the reference positions.

Configuration and operations other than the above, of the particle beam irradiation equipment 200, are similar to those in the configuration and the operations of the particle beam irradiation equipment 100 of Embodiment 1 shown in FIG. 1 and FIG. 5, so that the same reference numerals are given to the same parts and description thereof is omitted here.

As described above, in the particle beam irradiation equipment 200 according to Embodiment 2 of the invention, the control unit 2 causes the storage unit 3, at the time of the first alignment, to prestore the position information about the measured positions, attitudes and the like, of the electromagnets 1 (1A, 1B), and then acquires the displacement amounts, based on the position information as the reference positions stored in the storage unit 3, and from the position information of the electromagnets 1 (1A, 1B) acquired by the deformation simulator 4 at the time of the realignment. Thus, it is possible to easily adjust the positions, attitudes and the like, of the electromagnets even if the building deforms due to seasonal variation in outside air, crustal movement or the like.

In addition, because all the deformation amounts of the building, the apparatuses and the like are calculated using the deformation simulator 4, even if the main electromagnet placed on the upstream side of the HEBT system line and the electromagnet placed on the downstream side thereof are distantly positioned, for example, they are placed on different floors in the building, it is possible to precisely adjust the electromagnets while keeping their relative positions, attitudes and the like. This makes it possible to achieve highly-precise beam irradiation.

It is noted that, in Embodiment 2, the position information at the time of the realignment of the electromagnets 1 (1A, 1B) is acquired by the deformation simulator 4, at the time of the realignment; however, this is not limitative. The displacement amounts of the electromagnets 1 (1A, 1B) may be estimated at the time of the first alignment, based on the position information that is the reference positions stored in the storage unit 3. This also allows to recognize the time when the realignment becomes necessary, thus making it possible to create a plan for realignment beforehand.

Embodiment 3

In Embodiment 1, a case has been shown in which the position information at the time of the realignment is acquired by the cameras 10, whereas in Embodiment 3, a case will be shown in which that information is acquired by a GPS receiver.

Figure 8:
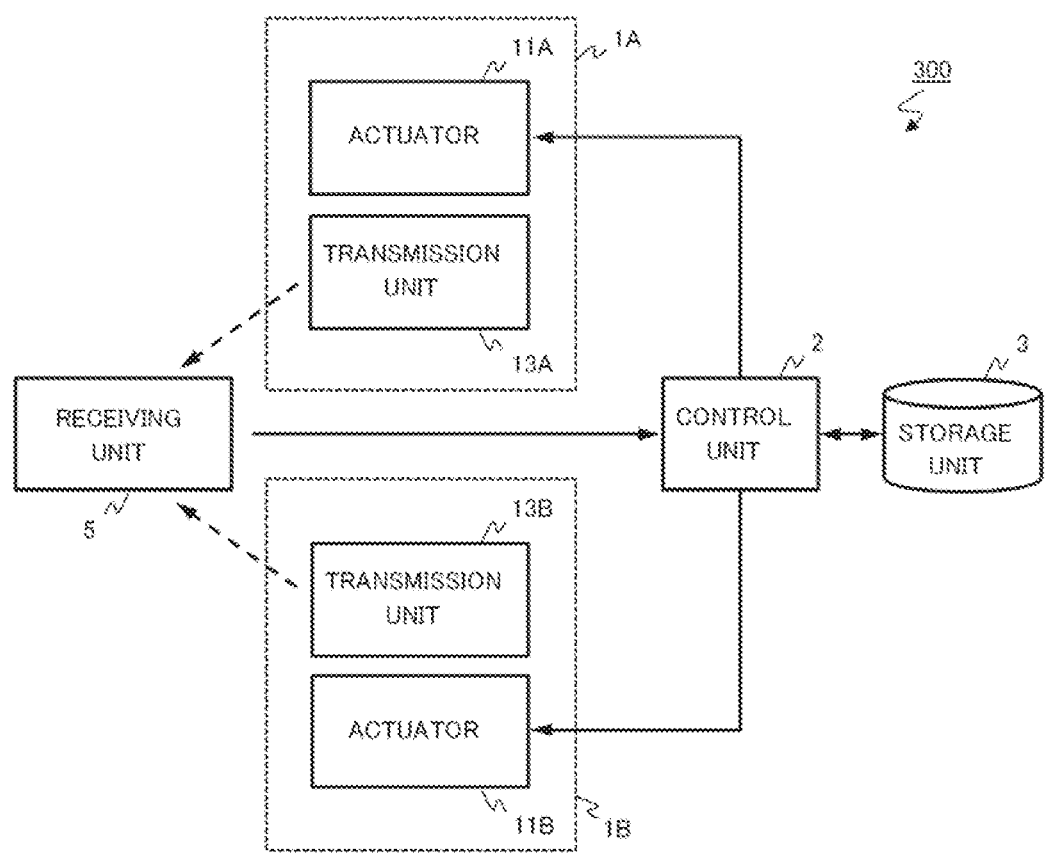
FIG. 8 is a block diagram showing a configuration of particle beam irradiation equipment according to Embodiment 3 of the invention.
Figure 9:
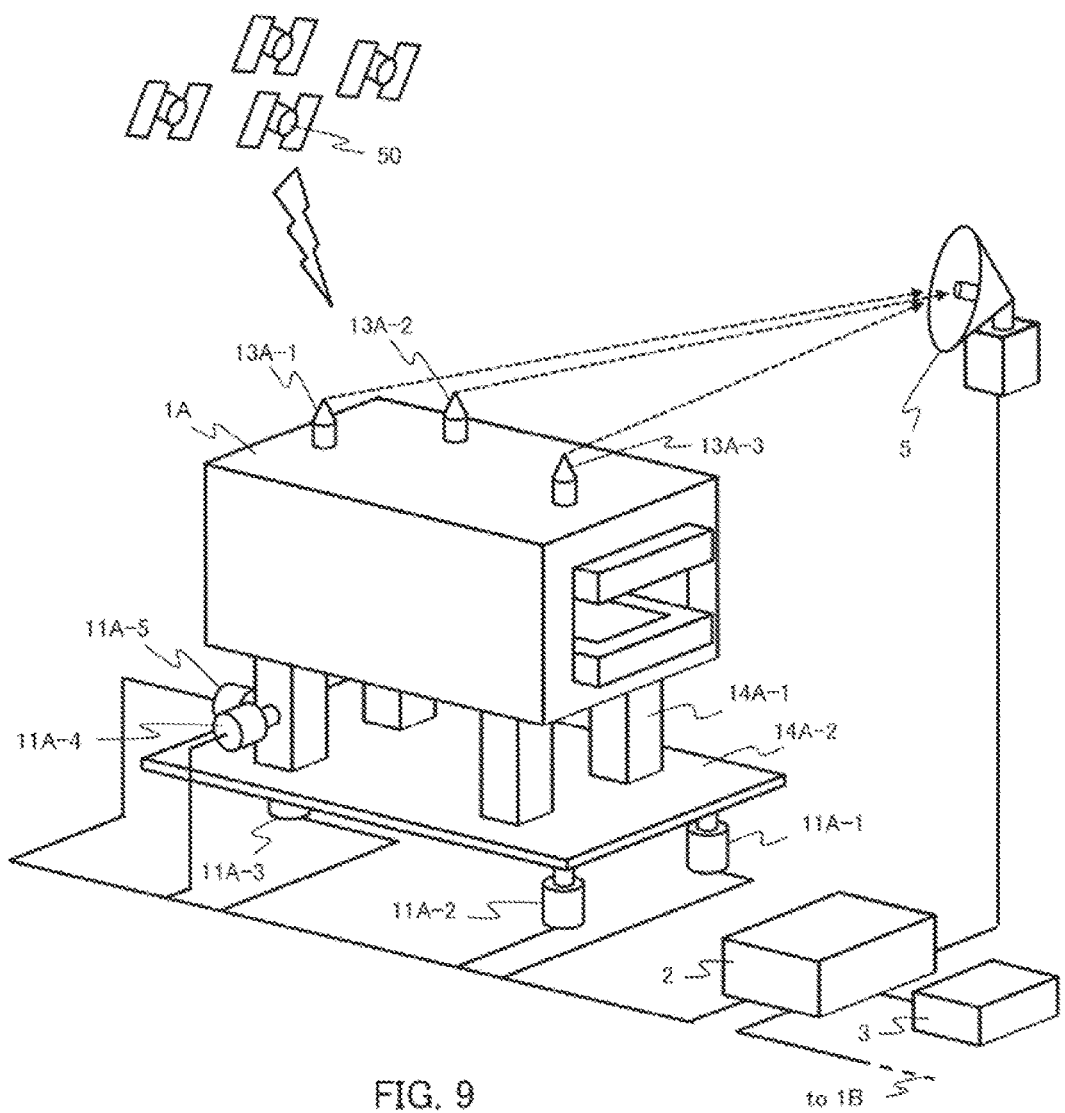
FIG. 9 is a perspective view showing an external appearance of the particle beam irradiation equipment according to Embodiment 3 of the invention.

FIG. 8 is a block diagram showing a configuration of particle beam irradiation equipment 300 according to Embodiment 3 of the invention. FIG. 9 is an external view of an electromagnet 1A for particle beam irradiation system, which is provided with the particle beam irradiation equipment 300.

As shown in FIG. 8 and FIG. 9, the particle beam irradiation equipment 200 includes a GPS receiver 5 serving as a receiving unit, in place of the cameras 10 (10-1, 10-2, . . . , 10-n) serving as a measurement unit in Embodiment 1. Further, the equipment includes CPS transmitters 13 (13A, 13B) each serving as a transmission unit, in place of the targets 12 (12A, 12B) in Embodiment 1. Three number of the GPS receivers 13 (13A, 13B) are provided on each of the electromagnets 1 (1A, 1B), and each determine its own position through observation of the position or the like by the multiple GPS satellites 50, and then transmit the position information thereof. The transmitted position information from the GPS transmitters 13 (13A, 13B) is received by the GPS receiver 5 placed at an original point in the building (for example, at a center point of the synchrotron). When the position information transmitted from the respective sets of three GPS transmitters 13 (13A, 13B) is received, the position of the GPS receiver 5 viewed from the electromagnets 1 (1A, 1B) having the respective sets of three GPS transmitters 13 (13A, 13B) is determined. When back calculation is applied using the position of the GPS receiver 5 as the original point, it is possible to calculate the relative positions, attitudes and the like, of the electromagnet 1A and the electromagnet 1B at the time the GPS receiver 5 is regarded as a reference.

At the time of the first alignment, the control unit 2 receives, using the GPS receiver 5, the position information transmitted from the GPS transmitters 13 (13A, 13B), and calculates the positions, attitudes and the like, of the electromagnets 1 (1A, 1B) using the position of the GPS receiver 5 as the original point, to thereby acquire the position information at the time of the first alignment. Also at the time of the realignment, likewise, the control unit receives, using the GPS receiver 5, the position information transmitted from the GPS transmitters 13 (13A, 13B), and calculates the positions, attitudes and the like, of the electromagnets 1 (1A, 1B) using the position of the GPS receiver 5 as the original point, to thereby acquire the position information at the time of the realignment.

In this manner, when the position information of the electromagnets 1 (1A, 1B) is acquired, using the position of the GPS receiver 5 as the original point, from the position information transmitted from the GPS transmitters 13 (13A, 13B), even if the main electromagnet 1A placed on the upstream side of the HEBT system line and the other main electromagnet 1B placed on the downstream side of the HEBT system line are positioned on different floors in the building, it is possible to easily recognize the relative positions, attitudes and the like, of the electromagnet 1A and the electromagnet 1B.

Configuration and operations other than the above, of the particle beam irradiation equipment 300, are similar to those in the configuration and the operations of the particle beam irradiation equipment 100 of Embodiment 1 shown in FIG. 1 and FIG. 5, so that the same reference numerals are given to the same parts and description thereof is omitted here.

As described above, in the particle beam irradiation equipment 300 according to Embodiment 3 of the invention, the control unit 2 causes the storage unit 3, at the time of the first alignment, to store as position information of the reference positions, the position information of the electromagnets 1 (1A, 1B) acquired from the position information transmitted from the GPS transmitters 13 (13A, 13B), using the position of the GPS receiver 5 as the original point, and then acquires the displacement amounts, based on the position information of the reference positions stored in the storage unit 3, and from the position information of the electromagnets 1 (1A, 1B) acquired from the position information transmitted from the GPS transmitters 13 (13A, 13B), at the time of the realignment, using the position of the GPS receiver 5 as the original point. Thus, it is possible to easily adjust the positions, attitudes and the like, of the electromagnets even if the building deforms due to seasonal variation in outside air, crustal movement or the like.

In addition, because the position information of the respective electromagnets 1 (1A, 1B) is acquired using the GPS receiver 5 and using the position of the GPS receiver 5 as the original point, even if the main electromagnet placed on the upstream side of the HEBT system line and the electromagnet placed on the downstream side thereof are distantly positioned, for example, they are placed on different floors in the building, it is possible to precisely adjust the electromagnets while keeping their relative positions, attitudes and the like. This makes it possible to achieve highly-precise beam irradiation.

It is noted that, in Embodiments 1 to 3, there is described that the positions, attitudes and the like, of the electromagnet 1A and the electromagnet 1B are both adjusted; however, this is not limitative. When either one of the electromagnet 1A and the electromagnet 1B is adjusted so that their relative positions and attitudes are kept, this also makes it possible to achieve highly-precise beam irradiation. In the alignment of the electromagnets, when they are placed on different floors in the building, it is general that the electromagnet nearer to the ground is not moved but the electromagnet on the upper floor, which is easily influenced by expansion/contraction of the building, is solely adjusted so that their relative positions are unchanged.

It should be noted that unlimited combination of the respective embodiments, and appropriate modification and omission in the embodiments may be made in the present invention without departing from the scope of the invention.

DESCRIPTION OF REFERENCE NUMERALS AND SIGNS 1, 1A, 1B: electromagnet, 2: control unit, 3: storage unit, 4: analysis unit, 5: GPS receiver, 10, 10-1, 10-2, . . . , 10-n: camera, 11, 11A, 11A-1, 11A-2, 11A-3, 11A-4, 11A-5, 11B, 11B-1, 11B-2, 11B-3, 11B-4, 11B-5: actuator, 12, 12A, 12A-1, 12A-2, 12A-3, 12A-4, 12B, 12B-1, 12B-2, 12B-3, 12B-4: target, 13, 13A, 13A-1, 13A-2, 13A-3, 13B, 13B-1, 13B-2, 13B-3: GPS transmitter, 100, 200, 300: particle beam irradiation equipment.

The invention claimed is:

1. Particle beam irradiation equipment comprising:
a first electromagnet provided on an upstream side of a high-energy-beam irradiation-system line;
a second electromagnet provided on a downstream side of the high-energy-beam irradiation-system line;
a position information acquisition unit that acquires position information of the first electromagnet and the second electromagnet;
a storage unit in which the position information of the first electromagnet and the second electromagnet, at the time of their first alignment, is prestored as relative reference position information, wherein the relative reference position information defines a relative relationship in position and attitude between the first electromagnet and the second electromagnet;
an adjustment mechanism that adjusts positions and attitudes of the first electromagnet and the second electromagnet; and
a control unit that calculates, based on the relative reference position information stored in the storage unit, and from position information of the first electromagnet and the second electromagnet acquired at the time of their realignment by the position information acquisition unit, displacement amounts of positions and attitudes of the first electromagnet and the second electromagnet occurring from the time of the first alignment to the time of the realignment, and controls/adjusts using the adjustment mechanism, the positions and attitudes of the first electromagnet and the second electromagnet according to the displacement amounts.

2. The particle beam irradiation equipment according to claim 1, wherein the control unit adjusts the position and attitude of either one of the first electromagnet and the second electromagnet, to thereby control relative positions and attitudes of the first electromagnet and the second electromagnet.

3. The particle beam irradiation equipment according to claim 2, wherein: the position information acquisition unit comprises a plurality of stereo cameras; the stereo cameras are so arranged that angles of view of respective adjacent stereo cameras among them are overlapped with each other; and the position information acquisition unit acquires the position information of the first electromagnet and the second electromagnet in such a manner that position coordinates of the adjacent stereo cameras are converted so that their coordinate systems are matched to each other, on the basis of position coordinates of at least four targets placed in the angles of view.

4. The particle beam irradiation equipment according to claim 2, wherein the position information acquisition unit comprises a deformation simulator, and acquires the position information of the first electromagnet and the second electromagnet through calculation, using the deformation simulator.

5. The particle beam irradiation equipment according to claim 2, wherein the position information acquisition unit comprises GPS transmitters and a GPS receiver; the GPS transmitters comprise at least three GPS transmitters placed on each of the first electromagnet and the second electromagnet; the GPS receiver is solely placed and acquires the position information of the first electromagnet and the second electromagnet transmitted from the GPS transmitters; and the control unit calculates the displacement amounts of positions and attitudes of the first electromagnet and the second electromagnet, from the position information received by the GPS receiver, using a position of the GPS receiver as a reference.

6. The particle beam irradiation equipment according to claim 2, wherein the first electromagnet and the second electromagnet are respectively placed on different floors in a building.

7. The particle beam irradiation equipment according to claim 1, wherein: the position information acquisition unit comprises a plurality of stereo cameras; the stereo cameras are so arranged that angles of view of respective adjacent stereo cameras among them are overlapped with each other; and the position information acquisition unit acquires the position information of the first electromagnet and the second electromagnet in such a manner that position coordinates of the adjacent stereo cameras are converted so that their coordinate systems are matched to each other, on the basis of position coordinates of at least four targets placed in the angles of view.

8. The particle beam irradiation equipment according to claim 1, wherein the position information acquisition unit comprises a deformation simulator, and acquires the position information of the first electromagnet and the second electromagnet through calculation, using the deformation simulator.

9. The particle beam irradiation equipment according to claim 7, wherein the first electromagnet and the second electromagnet are respectively placed on different floors in a building.

10. The particle beam irradiation equipment according to claim 8, wherein the first electromagnet and the second electromagnet are respectively placed on different floors in a building.

11. The particle beam irradiation equipment according to claim 1, wherein the position information acquisition unit comprises GPS transmitters and a GPS receiver; the GPS transmitters comprise at least three GPS transmitters placed on each of the first electromagnet and the second electromagnet; the GPS receiver is solely placed and acquires the position information of the first electromagnet and the second electromagnet transmitted from the GPS transmitters; and the control unit calculates the displacement amounts of positions and attitudes of the first electromagnet and the second electromagnet, from the position information received by the GPS receiver, using a position of the GPS receiver as a reference.

12. The particle beam irradiation equipment according to claim 11, wherein the first electromagnet and the second electromagnet are respectively placed on different floors in a building.

13. The particle beam irradiation equipment according to claim 1, wherein the first electromagnet and the second electromagnet are respectively placed on different floors in a building.

* * * * *